(12) United States Patent
Bedbury et al.

(10) Patent No.: US 6,552,237 B1
(45) Date of Patent: Apr. 22, 2003

(54) GRIGNARD PREPARATION OF UNSATURATED ORGANIC COMPOUNDS

(75) Inventors: Curtis J. Bedbury, Midland, MI (US); Binh T. Nguyen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/117,425

(22) Filed: Apr. 4, 2002

(51) Int. Cl.[7] ............................................. C07C 33/03
(52) U.S. Cl. .................. 568/909.5; 585/612; 260/665 G
(58) Field of Search .................. 260/665 G; 568/909.5; 585/612

(56) References Cited

U.S. PATENT DOCUMENTS

| | | | |
|---|---|---|---|
| 3,264,360 A | * | 8/1966 | Nudenberg |
| 5,242,625 A | * | 9/1993 | Jones |
| 5,596,120 A | | 1/1997 | Bank et al. |

FOREIGN PATENT DOCUMENTS

| | | |
|---|---|---|
| EP | 0729931 | 9/1996 |

OTHER PUBLICATIONS

Coates, et al., Organometallic Compounds, vol. 1, pp. 76–103 (1967) Methuen and Co. Ltd., London, U.K.
Kirk/Othmer, Encyclopedia of Chemical Technology, vol. 10, 721–734, (1966), The Interscience Encyclopedia, Inc., NY, N.Y.
Turk, et al, Organic Systhesis, vol. 27, 7–8 (1947).

* cited by examiner

*Primary Examiner*—Michael L. Shippen
(74) *Attorney, Agent, or Firm*—Robert L. McKellar

(57) ABSTRACT

A Grignard-type process for the preparation of unsaturated organic compounds. The process comprises contacting an unsaturated organic halide with magnesium metal in a mixture of ether and a polar halogenated hydrocarbon co-solvent, filtering the reaction product from the reaction step and thereafter, treating the reaction product filtrate from the filtration step to obtain the desired unsaturated organic compounds.

6 Claims, No Drawings

GRIGNARD PREPARATION OF UNSATURATED ORGANIC COMPOUNDS

The present invention relates to a Grignard-type process for the preparation of unsaturated organic compounds. The process comprises contacting an unsaturated organic halide with magnesium metal in a mixture of ether and a polar halogenated hydrocarbon co-solvent, filtering the reaction product from the reaction step and thereafter, treating the reaction product filtrate from the filtration step to obtain the desired unsaturated organic compounds.

The inventors of the present invention have found that the use of halogenated solvents in conjunction with ethers, the traditional Grignard reaction solvents, results in lower reaction temperatures, the ability to separate the desired unsaturated organic compounds from the by-produced magnesium halides with ease which results in higher yields of purer unsaturated organic compounds.

BACKGROUND OF THE INVENTION

The reaction of organic halides with magnesium metal in the presence of oxygenated solvents such as dialkyl ethers to form reactive complexes typically referred to as Grignard reagents is well known. The production and reactions of Grignard reagents has been the subject of books and numerous review articles. Such reviews are provided, for example, in Coates, et al., ORGANOMETALLIC COMPOUNDS, Vol. 1, pp. 76–103, (1967), Methuen and Co. Ltd, London, U.K.; and in Kirk/Othmer, ENCYCLOPEDIA OF CHEMICAL TECHNOLOGY, Vol. 10, 721–734 (1966), The Interscience Encyclopedia, Inc., NY, N.Y. The structure of the Grignard reagent has not been determined with certainty, however it is generally believed that the Grignard reagent exists as a complex in solution and that solvent can play a critical role in such complex formation. The unpredictable effect of solvent on the formation and reactivity of Grignard reagents is discussed in the above cited review articles, and the inventors herein believe, but should not be held to such a theory, that the following reaction equations may be the actual mechanisms, using allyl chloride as the organic halide reactant example:

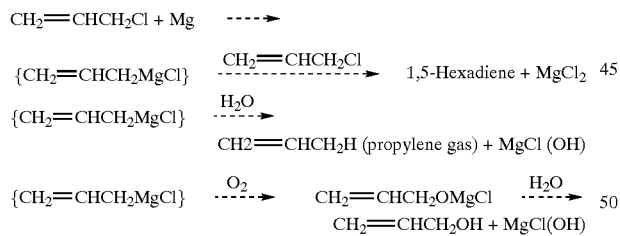

The preparation of unsaturated organic compounds such as 1,5-hexadiene by a process using a Grignard reagent as an intermediate is known. For example, Turk, et al., Organic Synthesis, Vol. 27, 7–8, 1947, teach a process for preparing 1,5-Hexadiene by the reaction of allyl chloride in anhydrous ether with magnesium turnings. Turk et al. teach that this reaction results in the formation of a thick slurry that becomes unstirrable. This unstirrable slurry is then treated with a hydrochloric acid solution until enough of the chloride by-product is in solution and then the slurry becomes sufficiently fluid to be stirred.

Such processes as taught by Turk et al. are not generally acceptable as a commercial process. The formation of the unstirrable slurry during the reaction can cause reduced mass transfer and heat transfer and therefore reduced yields. Furthermore, the nature of the slurry makes it necessary to treat the slurry in an additional step with a reagent to solubilize the slurry to allow isolation of the product. Typically, a major portion of the product is trapped with the unstirrable slurry. In addition, the non-flowable nature of the slurry does not allow for the reaction to be run as a large scale or continuous process.

A further disclosure regarding the use of the Grignard technology to prepare unsaturated organic compounds can be found in U.S. Pat. No. 5,596,120, that issued to Bank, et al., on Jan. 21, 1997 in which an attempt is made to overcome the drawbacks of the Turk, et al. process. Therein, Bank et al. teach that organosilanes can be prepared using magnesium metal with a mixture comprising an organic halide and a halosilane in a co-solvent comprising about one to 15 mole of a dialkyl ether comprising less than seven carbon atoms, per mole of allyl chloride, and about 0.05 to less than two mole of a liquid aromatic hydrocarbon solvent per mole of the dialkyl ether, at a temperature within a range of about 5° C. to 200° C. The taught hydrocarbon solvent is toluene. No mention is made in this disclosure about the use of chlorinated hydrocarbon solvents and the benefits achieved by their use in the Grignard technology.

Another disclosure is that found in European Patent Specification EP 0 729 931 to Hayes II, et al., in which there is disclosed a one-step Grignard-type process for the preparation of 1,5-Hexadiene. The process comprises contacting magnesium metal with a mixture comprising allyl chloride; one to 15 mole of a dialkyl ether comprising less than seven carbon atoms, per mole of the allyl chloride; and 0.05 to less than two mole of a liquid aromatic hydrocarbon solvent per mole of the dialkyl ether at a temperature within a range of 5° C. to 200° C. The liquid aromatic hydrocarbon solvent is disclosed as toluene and there is no mention in this disclosure with regard to the use of chlorinated hydrocarbon solvents for use in preparing unsaturated organic compounds. It is alleged that this process provides easily stirred slurries which improve mass transfer and heat transfer during the process and allows for easier separation of the unsaturated organic compound from the product slurry. Furthermore, it is noted therein, that the method allows for the process to be run as a continuous process.

THE INVENTION

The present invention thus deals with a process of preparing unsaturated organic compounds using a Grignard-type reaction technology wherein magnesium metal is contacted with an unsaturated organic halide in the presence of an ether and a polar halogenated hydrocarbon co-solvent or a mixture of ether and a mixture of polar halogenated hydrocarbon co-solvents.

Thus, what is disclosed and claimed herein is a method for the preparation of unsaturated organic compounds wherein the method comprises contacting an unsaturated organic halide with magnesium metal in a mixture of ether and a polar halogenated hydrocarbon co-solvent or a mixture of ether and a mixture of polar halogenated hydrocarbon co-solvents to produce the unsaturated organic compound. Thereafter, filtering the reaction product and treating the reaction product filtrate to obtain the desired unsaturated organic compounds.

A further embodiment of this invention is a method for the preparation of unsaturated organic compounds wherein the method comprises contacting an unsaturated organic halide with magnesium metal in a mixture of ether and a polar halogenated hydrocarbon co-solvent or a mixture of ether and a mixture of polar halogenated hydrocarbon co-solvents wherein the temperature is in the range of from 5° C. to 200° C. and most preferred range is from 50° C. 100° C., and the pressure is in the range of from ambient pressure to about 200 psig wherein the most preferred range is from 0 psig to about 125 psig.

Both of these embodiments are known as "one-step" processes for the preparation of unsaturated organic compounds because it is not necessary to isolate an intermediate Grignard-type reagent in the process and then further react this Grignard-type reagent with the unsaturated organic halide to form the unsaturated organic compounds. Further, it is not necessary to conduct a separate solubilization step on the resulting product slurry to facilitate recovery of the unsaturated organic compound.

The magnesium metal used in this invention can be any of the known forms of the metal that are currently used for Grignard-type reactions. For example, the metal can be any of those known in the art that are in the form of powder, flakes, granules, chips, lumps, and shavings, and the like.

Contact of the magnesium metal with the unsaturated organic halide can be undertaken in standard type reactors suitable for running Grignard type reactions. The reactor can be a batch, semi-batch, or continuous type of reactor. A preferred reactor is a continuous reactor. The environment in which the present method is carried out should be inert for best results. Therefore, in a preferred method, the reactor is purged and blanketed with an inert gas such as, for example, nitrogen or argon.

Generally, the magnesium metal is placed in the reactor containing a co-solvent mixture. The unsaturated organic halide in additional co-solvent is then fed to the reactor at a controlled rate. The mole ratio of magnesium to the unsaturated organic halide fed to the reactor is not critical and can be varied within wide limits. In a batch process, it is preferred that the final mole ratios of magnesium to unsaturated organic halide provide the unsaturated organic halide in sufficient excess to ensure essentially total conversion of the magnesium to the magnesium salts. When the present process is conducted as a continuous process, the magnesium metal is typically present in excess in relation to the unsaturated organic halide fed to the reactor. In such a case, the rate of feed of the unsaturated organic halide to the reactor can be controlled to ensure acceptable levels of conversion of the unsaturated organic halide to the unsaturated organic compounds and, minimal presence of the unreacted unsaturated magnesium halide complexes. Any excess unsaturated organic halide can be captured and recycled to the reactor.

Unsaturated organic halides useful in this invention are described by the formula RX, wherein R is an unsaturated hydrocarbon group comprising about one to 12 carbon atoms and X is selected from a group consisting of chlorine and bromine atoms. The preferred substituent X for the unsaturated organic halide is the chlorine atom. The substituent R can be a substituted or unsubstituted unsaturated hydrocarbon group comprising one to 12 carbon atoms. The substituent R can be, for example, alkenyl or cycloalkenyl. Specific examples of R substituents include vinyl, allyl, hexenyl, pentenyl, cyclopentyl, and cyclopentenyl. Preferred for this invention is the substituent allyl wherein the most preferred unsaturated organic halide is allyl chloride.

The dialkyl ethers useful in this invention include, for example, dimethyl ether, diethyl ether, ethylmethyl ether, n-butylmethyl ether, n-butylethyl ether, di-n-butyl ether, di-isobutyl ether, isobutylmethyl ether, and isobutylethyl ether, and the like. The preferred ether is diethyl ether. It is preferred that the amount of ether in the co-solvent mixture be as small as is possible and therefore, it is preferred that the ratio of ether to the polar halogenated hydrocarbon co-solvent be in the range of about 0.2:2 to 0.5:2.

The polar halogenated hydrocarbon solvent can be any polar halogenated hydrocarbon solvent that is a liquid under process conditions. The polar halogenated hydrocarbon solvent can be, for example, halogenated aromatic solvents, or a combination of them, or aliphatic halogenated solvents, or a combination of them, or a combination of aromatic and aliphatic halogenated hydrocarbons. Preferred for this invention are the aromatic halogenated solvents, and most preferred is chlorobenzene. It should be noted that when any aliphatic halogenated solvent is used, it should be an aliphatic halogenated solvent that reacts with magnesium slower than the formed Grignard reagent since the aliphatic halogenated compounds are more reactive than the aromatic halogenated compounds.

The mole ratio of the dialkyl ether to the polar halogenated solvents is critical to the present process. The present method requires that the amount of ether that is present be as low as possible, meaning that a high ratio of the halogenated solvent to the ether is desired. This is because it is believed by the inventors herein that the halogenated hydrocarbon solvent aids in the precipitation of the very fine $MgCl_2$ that is formed during the reaction and substantially aids in the removal of such salts. Thus, for purposes of this method, the ratio of the total ether to the halogenated solvents should be in the range of about 0.5:2 to 1:1.

The inventors herein have discovered that this method provides very low viscosity slurries from which the $MgCl_2$ can be separated easily and essentially completely that leads to substantial improvements in mass transfer and allows for a significant reduction in the total amount of solvent required for the reaction when compared to prior art methods. In addition, this method does not lead to isomerization or polymerization of the unsaturated materials. Generally, this method does not require an initiator for the reaction.

EXAMPLES

Grignard Test

The Grignard test reagent is a colorless solution of 100 mg of 2,2'-biquinoline in 50 ml of benzene. The presence of allyl Grignard reagent in the reaction mixture was confirmed by adding the reaction mixture (0.2 cc) to an indicator solution of this material in a toluene solution (0.2 cc). When allylMgCl is present, a red color mixture is observed. When all of the Grignard reagent has reacted or disappeared, a colorless mixture is observed.

Analysis of 1,5-Hexadiene Formation

The formation of 1,5-Hexadiene from a reaction was monitored periodically by gas chromatography with octane as the internal standard.

Grignard Apparatus

The apparatus to prepare 1,5-Hexadiene was a 29/40 3-necked, 1 liter, round bottom, glass flask that was equipped with a thirty inch Allihn reflux condenser with a 10 bulb configuration, a dry ice condenser surmounted on the top of the reflux condenser, a nitrogen purge system to provide inert nitrogen to the reaction environment, a heating mantle for the glass flask and a thermocouple connected to a Gardsman temperature control unit, along with an air stirrer mechanism to stir the contents of the glass flask.

Example 1
Comparison Example Against the Prior Art Using Ether as the Only Solvent The final molar ratio of ether to the allyl chloride was 16:1. Magnesium metal (1.82 grams, 0.08 mole) and anhydrous diethyl ether (33.6 grams, 0.47 mole) along with 3.07 grams, 0.08 mole) of n-octane were loaded into a 3-necked, 1 liter glass flask. At the beginning, a clear solution with magnesium metal was observed. The solution was then heated to ether reflux at about 32° C. From a 1 liter addition funnel, a solution of allyl chloride (16.59 , 0.21 mole), diethyl ether (84.73 grams, 1.17 mole) was slowly added to the refluxing ethereal mixture at a rate of about 8 to 10 drops/5 sec. to control the exotherm. The addition was completed in about thirty minutes. A "thickening" of the reaction mixture was observed and stirring became very difficult. Approximately thirty minutes after the addition was completed, a "paste" was obtained which due to the complexing of $MgCl_2$ or diethyl ether or diethyl ether->Mg<-R-Cl. The reaction mixture became unstirrable.

Example 2
Comparison Example Against Ether/Toluene as Co-solvents at a Mole Ratio of Ether/toluene/allylchloride of 3.21/14.88/1.05

Magnesium metal (12.15 grams, 0.5 mole), anhydrous diethyl ether (178.4 grams 2.41 mole), toluene (1295.68 grams 14.07 mole) and n-octane (26.33 grams) were loaded into a 3-necked 1 liter flask. In the beginning, a clear solution with magnesium metal was observed. The solution was then heated to ether reflux at about 32°–34° C. From a one liter addition funnel, a solution of allyl chloride (81.85 grams, 1.05 mole), diethyl ether (59.5 grams, 0.80 mole) and toluene (74.5 grams 0.81 mole) was slowly added to the refluxing ether/toluene solution at a rate of about 10 to 12 drops/5 sec., to control the exotherm. At this time, within minutes, the reaction temperature increased to 36 to 37° C. and a cloudy solution was observed. Approximately 8 minutes after the addition, the hazy/cloudy solution began to clear. The reaction mixture continued to change color to a milky white mixture that was due to the formation of $MgCl_2$ from the reaction of the allyl chloride with the magnesium. This material precipitated from the reaction mixture. The Grignard test at this time showed the presence of allylMgCl. Gas Chromatography analysis showed about 20% 1,5-Hexadiene had been formed. It took approximately 0.5 hours to complete the addition and the reaction temperature still remained at about 34° C.

The Grignard test was used to continue to periodically check the disappearance of the allylMgCl. The formation of 1,5-Hexadiene from the reaction was also monitored periodically by gas chromatography analysis with octane as the internal reference. The yield of 1,5-Hexadiene was greater than 91% after 5.7 hours. The $MgCl_2$ salt formed under these conditions was a free flowable solid that readily precipitated from solution and could be easily dispersed even after standing a few days on the bench top at room temperature. Upon standing at room temperature for several days, a second layer of a very fine $MgCl_2$ precipitated slowly from the solution. This precipitate was carried in the solution throughout the process and caused distillation and other operational problems by its presence.

Example 3
Ether/chlorobenzene as Co-solvents at a Mole Ratio of Ether/chlorobenzene/allylchloride of 3/3/1

Magnesium metal (12.15 grams, 0.5 mole), anhydrous diethyl ether (178.4 grams, 2.4 mole), chlorobenzene (239.62 grams, 2.12 mole) and n-octane (26.33 grams, 0.23 mole) were loaded into a 3-necked,1 liter glass flask. At the beginning, a clear solution with magnesium metal was observed. The solution was then heated to ether reflux at about 32 to 34° C. From a 1 liter addition funnel, a solution of allyl chloride (81.85 grams, 1.05 mole), diethyl ether (59.5 grams 0.08 mole) and chlorobenzene (91.2 grams, 0.81 mole) was added slowly to the refluxing solution at a rate of approximately 10 to 12 drops/5 seconds to control the exotherm. At this time, within minutes, the reaction temperature went to 36 to 37° C. and a cloudy solution was observed. Approximate 8 to 10 minutes into the addition, the hazy/cloudy solution begin to clear. The reaction mixture continued to change color to a milky mixture that was due to the formation of magnesium chloride from the reaction of the allyl chloride with the magnesium metal, which precipitated from the solution. The Grignard test at this time showed the presence of allylMgCl. It took approximate 5.5 hours to complete the addition.

The Grignard test was used periodically checked to determine the disappearance of allylMgCl. The formation of 1,5-Hexadiene from the reaction was monitored periodically by gas chromatography of the reaction mixture with octane as the internal reference.

The $MgCl_2$ salt formed under these conditions was a free flowable solid that readily separated from solution and could easily be dispersed after several days standing at room temperature. Upon standing at room temperature for several days, a second layer of very fine $MgCl_2$ that had formed, disappeared. A gas chromatography analysis showed that the reaction did not make allylbenzene.

What is claimed is:

1. A method for the preparation of unsaturated organic compounds, the method comprising:

(I) contacting an unsaturated organic halide with magnesium metal in a mixture of ether and a polar halogenated hydrocarbon co-solvent or a mixture of ether and a mixture of polar halogenated hydrocarbon co solvents;

(II) filtering the reaction product from step (I);

(III) treating the reaction product filtrate from step (II) to obtain the desired unsaturated organic compounds.

2. A method for the preparation of unsaturated organic compounds, the method comprising:

(A) contacting an unsaturated organic halide with magnesium metal in a mixture of ether and a polar halogenated hydrocarbon co-solvent or a mixture of ether and a mixture of polar halogenated hydrocarbon co-solvents wherein:

(i) the temperature is in the range from 5° C. to 200° C., and (ii) the pressure is in the range from ambient pressure to about 200 psig.

3. A method as claimed in claim 2, wherein the organic halide is allyl chloride, the ether is diethylether and the polar halogenated hydrocarbon co-solvent is chlorobenzene.

4. A method as claimed in claim 1 wherein the ratio of the ether to the total halogenated co-solvents to the organic halide is 1:5:1 to 4:2:1.

5. A method as claimed in claim 1 wherein the polar halogenated hydrocarbon co-solvent is selected from the group consisting essentially of (i) aromatic halogenated hydrocarbons, (ii) aliphatic halogenated hydrocarbons, and (iii) mixtures of (i) and (ii).

6. A method as claimed in claim 1 wherein the ratio of ether to the polar halogenated co-solvent is 0.2:2 to 0.5:2.

* * * * *